US009417220B2

(12) United States Patent
Wang et al.

(10) Patent No.: US 9,417,220 B2
(45) Date of Patent: Aug. 16, 2016

(54) INTEGRATED HYDROCARBON ANALYSIS

(71) Applicants: Frank C. Wang, Annandale, NJ (US); Kuangnan Qian, Skillman, NJ (US); Kathleen E. Edwards, Freehold, NJ (US)

(72) Inventors: Frank C. Wang, Annandale, NJ (US); Kuangnan Qian, Skillman, NJ (US); Kathleen E. Edwards, Freehold, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 332 days.

(21) Appl. No.: 14/061,086

(22) Filed: Oct. 23, 2013

(65) Prior Publication Data

US 2015/0107331 A1    Apr. 23, 2015

(51) Int. Cl.
| | |
|---|---|
| *G01N 30/90* | (2006.01) |
| *G01N 30/72* | (2006.01) |
| *G01N 30/46* | (2006.01) |
| *G01N 30/86* | (2006.01) |
| *G01N 33/28* | (2006.01) |
| *H01J 49/16* | (2006.01) |
| *H01J 49/44* | (2006.01) |

(52) U.S. Cl.
CPC .............. *G01N 30/72* (2013.01); *G01N 30/463* (2013.01); *G01N 30/7206* (2013.01); *G01N 30/8682* (2013.01); *G01N 33/28* (2013.01); *H01J 49/168* (2013.01); *H01J 49/446* (2013.01)

(58) Field of Classification Search
CPC .  G01N 30/02; G01N 2030/027; G01N 30/00; G01N 30/72; A61K 2300/00; B01D 15/3833

USPC .......... 73/23.37, 1.02, 61.52; 210/198.2, 656; 436/16

See application file for complete search history.

(56) References Cited

U.S. PATENT DOCUMENTS

| | | | | |
|---|---|---|---|---|
| 4,826,603 | A * | 5/1989 | Hayes, Jr. ............ | G01N 30/461 210/635 |
| 5,644,129 | A * | 7/1997 | Hsu ........................ | H01J 49/168 250/282 |
| 7,598,487 | B2 | 10/2009 | Qian et al. | |
| 8,027,792 | B2 * | 9/2011 | Bertoncini ............. | G01N 30/86 702/24 |
| 8,301,397 | B2 * | 10/2012 | Bertoncini ........... | G01N 30/463 702/24 |
| 2003/0089663 | A1 * | 5/2003 | Petro .................. | B01D 15/1878 210/656 |

(Continued)

OTHER PUBLICATIONS

PCT Application No. PCT/US2014/058784, Communication from the International Searching Authority, Forms PCT/ISA/220, PCT/ISA/210 and PCT/ISA/237, dated Feb. 19, 2015, 14 pages.

(Continued)

*Primary Examiner* — Eric S McCall
*Assistant Examiner* — Mohammed E Keramet-Amircola
(74) *Attorney, Agent, or Firm* — Larry E. Carter; Glenn T. Barrett; Andrew T. Ward

(57) ABSTRACT

Petroleum or other hydrocarbon samples can be analyzed in parallel by 1) GC-field ionization Time of Flight Mass Spectrometer (GC-FI-TOF MS) and 2) two dimensional gas chromatography (2D-GC) equipped with a flame ionization detector (FID). The combined techniques allow for improved quantitative characterization of the compounds within a hydrocarbon sample. The techniques can be combined by correlating the 2D-GC FID data with the GC-FI-TOF MS data based on correlation of compound classes, correlation of retention windows within a compound class, correlation of individual compounds, such as paraffins, or a combination thereof.

15 Claims, 6 Drawing Sheets

(56) References Cited

U.S. PATENT DOCUMENTS

2007/0114377 A1* 5/2007 Qian ................ G01N 30/7206
250/282
2010/0206812 A1* 8/2010 Woods ................ C10G 21/00
210/656

OTHER PUBLICATIONS

C. Vendeuvre, R. Ruiz-Guerrero, F. Bertoncini, L. Duval, D. Thiebaut and M.C. Hennion, "Characterisation of middle-distillates by comprehensive two-dimensional gas chromatography (GCxGC): A powerful alternative for performing various standard analysis of middle-distillates", Journal of Chromatography, vol. 1086, No. 1-2, Sep. 9, 2005, pp. 21-28.

S.P. Pyl, Z. Hou, K.M. Van Geem, M.-F. Reyniers, G,B. Marin and M.T. Klein, "Modeling the Composition of Crude Oil Fractions Using Constrained Homologous Series", Industrial & Engineering Chemistry Research, vol. 50, No. 18, Sep. 21, 2011, pp. 10858-10858.

K.M. Van Geem, S.P. Pyl, M.-F. Reyniers, J. Vercammen, J. Beens and G.B. Marin, "On-line analysis of complex hydrocarbon mixtures using comprehensive two-dimensional gas chromatography", Journal of Chromatography, vol. 1217, No. 43, Oct. 22, 2010, pp. 6623-6633.

I.P. Androulakis et al., "An Integrated Approach for Creating Model Diesel Fuels", Energy & Fuels, vol. 19, No. 1, Sep. 19, 2004, pp. 111-119.

\* cited by examiner

| Z | COMPOUND TYPES | POSSIBLE CORE STRUCTURE(S) AND CORE MASS | | | | COMPOUND CLASSES |
|---|---|---|---|---|---|---|
| 2 | NORMAL PARAFFINS | | | | | PARAFFINS |
| 2 | ISO PARAFFINS | | | | | |
| 0 | 1-RING NAPHTHENES | | 84 | | | NAPHTHENES |
| -2 | 2-RING NAPHTHENES | | 138 | | | |
| -4 | 3-RING NAPHTHENES | | 192 | | | |
| -6 | BENZENES | | 78 | | | 1-RING AROMATICS |
| -8 | INDANES/NAPHTHENO BENZENES | | 118 | | 132 | |
| -10 | DINAPHTHENO BENZENES | | 186 | | | |
| -12 | NAPHTHALENES | | 128 | | | 2-RING AROMATICS |
| -14 | BIPHENYLS/ ACENAPHTHALENES | | 154 | | 154 | |
| -16 | FLUORENES/DINAPHTHENO NAPHTHALENES | | 166 | | 236 | |
| -18 | PHENANTHRENES/ ANTHRACENES | | 178 | | 178 | 3-RING AROMATICS |
| -20 | ACEPHENANTHRENES | | 190 | | | |
| -22 | PYRENES/FLUORANTHENES | | 202 | | 202 | 4-RING AROMATICS |
| -24 | CHRYSENES | | 228 | | | |
| -26 | ACECHRYSENES/NAPHTHENO CHRYSENES | | 240 | | 282 | |
| -28 | BENZOPYRENES/PERYLENES | | 252 | | 252 | 5-RING+ AROMATICS |
| -30 | BENZOCHRYSENES | | 278 | | | |
| -32 | NAPHTHENOBENZOCHRYSENES | | 332 | | | |
| -34 | DIBENZOPYRENES | | 302 | | | |

*FIG. 4*

| Z | IDENTIFICATION | POSSIBLE CORE STRUCTURE(S) AND CORE MASS | | COMPOUND CLASSES |
|---|---|---|---|---|
| +2 | SULFIDE/MERCAPTAN | ~S~  ~~SH | | ALIPHATIC SULFIDES |
| 0 | CYCLIC SULFIDE | | 102 | CYCLIC SULFIDES |
| -2 | DICYCLIC SULFIDE | | 156 | |
| -4 | THIOPHENES | | 84 | 1-RING AROMATIC SULFURS |
| -6 | BENZENE THIOLS | | 110 | |
| -8 | DINAPHTHENOTHIOPHENES | | 192 | |
| -10 | BENZOTHIOPHENES (BTs) | | 134 | 2-RING AROMATIC SULFURS |
| -12 | NAPHTHENO BTs | | 188 | |
| -14 | DINAPHTHENO BTs | | 242 | |
| -16 | DIBENZO-THIOPHENES (DBTs) | | 184 | 3-RING AROMATIC SULFURS |
| -18 | NAPHTHENO DBTs | | 238 | |
| -20 | BAY-S PHENANTHRENES | | 208 | |
| -22 | BENZO DBTs | | 234 | 4-RING AROMATIC SULFURS |
| -24 | NAPHTHENO BENZO DBTs | | 288 | |
| -26 | DINAPHTHENO BENZO DBTs | | 342 | |
| -28 | DIBENZO DBT | | 284 | 5-RING+ AROMATIC SULFURS |

*FIG. 5*

| Z | IDENTIFICATIONS | POSSIBLE CORE STRUCTURE(S) AND CORE MASS | COMPOUND CLASS |
|---|---|---|---|
| -14 | DITHIOPHENOBENZENES (DTBs) |  190 | 3-RING AROMATIC DISULFURS |
| -16 | NAPHTHENO DTBs |  244 | |
| -18 | DINAPHTHENO DTBs |  298 | |
| -20 | DITHIOPHENONAPHTHALENES (DTNs) |  240 | 4-RING AROMATIC DISULFURS |
| -22 | NAPHTHENO DTNs |  294 | |
| -24 | DINAPHTHENO DTNs |  348 | |
| -26 | DITHIOPHENOPHENANTHRENES (DTPs) |  290 | 5-RING+ AROMATIC DISULFURS |
| -28 | NAPHTHENO DTPs |  344 | |
FIG. 6

INTEGRATED HYDROCARBON ANALYSIS

FIELD OF THE INVENTION

This invention provides methods for characterizing the composition of petroleum or hydrocarbon fractions, such as distillate fractions or other fractions that can pass through a gas chromatography column.

BACKGROUND OF THE INVENTION

Petroleum samples are complicated hydrocarbon mixtures containing paraffins, cyclic paraffins, multiring aromatics, and various heteroatomic hydrocarbons (most commonly O, S, and N). Virgin petroleum crude oils contain molecules of a wide boiling point range from highly volatile $C_4$ hydrocarbons to nonvolatile asphaltenes. Analysis of petroleum composition of various boiling ranges is valuable for improving the operation of many subsequent processes.

Determining the composition of a petroleum sample can be beneficial for a variety of reasons. For example, the composition of a distillate boiling range sample can provide insight into the energy value of the sample as well as the cold flow properties.

U.S. Pat. No. 7,598,487 describes methods for characterizing the composition of a petroleum sample, such as a distillate sample. The sample is characterized using two types of techniques. One type of characterization is to use a gas chromatograph with a field ionization time-of-flight mass spectrometer to determine the identity of species within a sample. This chromatographic characterization is used in combination with another technique that can provide relative amounts of general classes of compounds within the sample. Supercritical fluid chromatography is described as an example of a technique for determining relative amounts of the compound classes in a sample.

SUMMARY OF THE INVENTION

In an embodiment, a method for characterizing petroleum or other hydrocarbon compositions is provided. The method includes separating a first plurality of compounds in a first hydrocarbon sample using a first gas chromatography separation; determining a composition and a first weight for each of the separated first plurality of compounds using mass spectrometry, the ions for mass spectrometry being formed by a soft ionization method; separating a second plurality of compounds in a second hydrocarbon sample using a second gas chromatography separation, the second gas chromatography separation including at least a first separation stage and a second separation stage, the second hydrocarbon sample being derived from the same hydrocarbon source as the first hydrocarbon sample; determining a second weight for each of the separated second plurality of compounds; assigning the separated second plurality of compounds to a plurality of compound classes; determining a relative weight for each of the plurality of compound classes based on the second weights of the assigned compounds for each compound class; normalizing the first weight for each of at least a portion of the first separated plurality of compounds, based on the determined relative weights for the plurality of compound classes, to generate a normalized weight for each compound, the normalizing of a first weight for a compound being based on at least a compound class corresponding to a determined composition for the compound; and developing a model of composition for the hydrocarbon source based on at least the normalized weights for the first separated plurality of compounds.

In another embodiment, a method for characterizing petroleum or other hydrocarbon compositions is provided. The method includes separating a first plurality of compounds in a first hydrocarbon sample using a first gas chromatography separation, each compound in the first plurality of compounds being within a retention normal-paraffin index window; determining compositions for the separated first plurality of compounds using mass spectrometry, the ions for mass spectrometry being formed by a soft ionization method; separating a second plurality of compounds in a second hydrocarbon sample using a second gas chromatography separation, the second gas chromatography separation including at least a first separation stage and a second separation stage, the second hydrocarbon sample being derived from the same hydrocarbon source as the first hydrocarbon sample, each compound in the second plurality of compounds corresponding to a compound in the first plurality of compounds, where each compound in the second plurality of compounds is within the same retention normal-paraffin index window as the corresponding compound in the first plurality of compounds; determining relative weights for the separated second plurality of compounds; correlating the first plurality of compounds with the second plurality of compounds; and developing a model of composition for the hydrocarbon source based on the correlation of the first plurality of compounds with the second plurality of compounds, and based on combining the determined compositions for the first plurality of compounds to provide a total composition.

Optionally, the methods can further include normalizing of a first weight for a compound based on a retention window corresponding to the determined compound. Optionally, the methods can further comprise identifying a composition for one or more paraffin compounds in the separated second plurality of compounds.

BRIEF DESCRIPTION OF THE FIGURES

FIGS. 4-6 show examples of assignments of compounds to Z-classes.

DETAILED DESCRIPTION OF THE EMBODIMENTS

Overview

Figure 1:
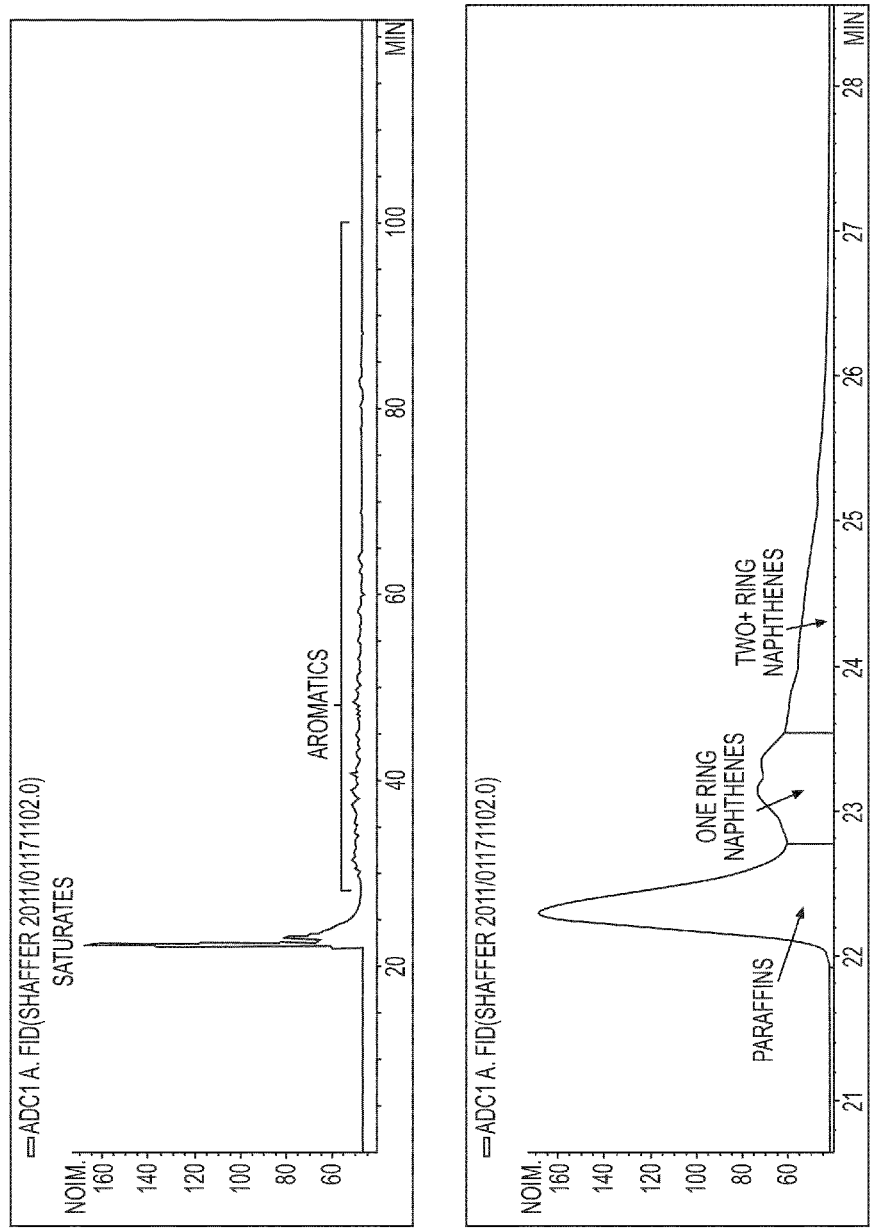
FIG. 1 shows a supercritical fluid chromatogram of a diesel boiling range sample.

In various aspects of the invention, petroleum or other hydrocarbon samples can be analyzed in parallel by 1) GC-field ionization Time of Flight Mass Spectrometer (GC-FI-TOF MS) and 2) two dimensional gas chromatography (2D-GC) equipped with a flame ionization detector (FID). The petroleum/hydrocarbon samples can be, for example, one or more samples from a whole crude, a total liquid product from a research or refinery process, or a fraction or intermediate stream from research or refinery process. If a sample has an upper boiling point less than 1050° F. (566° C.), a composition for the entire sample can be determined. If the samples contain 1050° F.+material, the 1050° F.+material may not be suitable for elution through a gas chromatography column. In this type of situation, the composition can be normalized based on the yield of the 1050° F.–material. The yield of the 1050° F.–material can be determined by 2D-GC-FID using a reference petroleum sample that is known to completely elute from the 2D-GC system.

In various aspects of the invention, molecular attributes and their quantities are determined by GC-FI-TOF MS. The total quantities of compound classes are also determined by 2D-GC. The sum of molecular attributes within a compound class are then normalized based on the quantity for the corresponding class determined by 2D-GC. Normal paraffin carbon number distributions can also be directly determined by 2D-GC.

GC-FI-TOF MS identifies molecules in the petroleum (or hydrocarbon) samples. In this technique, GC separates petroleum molecules by their boiling points and polarities. For the GC methods described herein, the eluted molecules were ionized near a field ionization emitter. In this type of ionization, an electron is removed from the petroleum molecule via a "quantum tunneling effect" to form molecular ions. The mass to charge ratios (m/z) of the molecular ions were then accurately measured. Since field ionization of petroleum molecules produces primarily singly charged ions, the molecular mass and m/z can be used interchangeably. Empirical molecular formulas ($C_cH_{2c+z}S_sN_nO_o$) were assigned to the molecular mass detected by the technique. Based on Z-numbers as defined in an assigned molecular formula, petroleum molecules can be grouped into paraffins, naphthenes, 1-ring aromatics, 2-ring aromatics, 3-ring aromatics, 4-ring aromatics and 5-ring+aromatics. (See Tables 2, 3 and 4 below for relationships between Z-numbers and compound classes.) Sulfur and di-sulfur molecules were grouped into corresponding hydrocarbon compound classes for normalization purpose. For example, benzothiophenes were included in total diaromatics. Also, aliphatic sulfides were grouped into saturated hydrocarbons classes, although these molecules do not strictly belong to those chemical classes.

2D-GC separates petroleum molecules into various compound classes and quantifies the total of compound classes by FID. In the 2D-GC methods described herein, the first dimension separated petroleum molecules by boiling point (primarily influenced by carbon number and heteroatom content). The second dimension of GC separated petroleum molecules by polarity (primarily influenced by aromaticity and heteratom function groups). The 2D-GC compound classes included paraffins, 1-ring naphthenes, 2-ring+naphthenes, 1-ring aromatics, 2-ring aromatics, 3-ring aromatics, 4-ring aromatics and 5-ring+aromatics. 2D-GC also allowed for determination of total normal paraffin concentrations and carbon number distributions. By analyzing a reference (a material that can completely elute from a 2D-GC system, such as diesel), a recovery or yield can be determined for the analyte samples.

Characterization of the compounds within a hydrocarbon fraction, such as a petroleum fraction, is an ongoing problem. A variety of mass spectrometry techniques are available that allow for qualitative determination of different types of compounds within a hydrocarbon sample. Depending on the nature of the detector, mass spectrometers can distinguish the molecular weights of compounds on the order of mDa. Since the weight of any given isotope (except for $^{12}C$, by definition) is not exactly an integer value of Daltons, the detection limits of mass spectrometers are sufficient to differentiate between any two compounds that have distinct atomic compositions.

Unfortunately, the detectors used in mass spectrometry require generation of ions for detection of species. For hydrocarbons, formation of ions from a sample is a challenging problem. "Soft ionization" methods exist that allow for at least some detection of most types of hydrocarbons without substantial fragmentation. However, these soft ionization methods can differ widely for how effectively a given type of hydrocarbon is ionized (i.e., response factor for a given hydrocarbon) both across different ionization methods and within a single ionization method. As a result, although mass spectrometric methods can provide qualitative information about the individual hydrocarbons within a sample, it is difficult to obtain quantitative information regarding the amounts of hydrocarbons to a desired degree of accuracy. Even obtaining information regarding relative amounts of hydrocarbons within a sample can be a challenge if a sample contains distinct classes of compounds, due to differences in ionization efficiency (response factor) between compounds from different classes such as paraffins and aromatics.

The methods described in U.S. Pat. No. 7,598,487 provide one option for addressing the above difficulties in characterizing a hydrocarbon fraction. In U.S. Pat. No. 7,598,487, field-ionization time-of-flight mass spectrometry is used to identify the various compounds present within a hydrocarbon sample. In order to determine the quantities of each compound, a technique such as supercritical fluid chromatography is used to generate a profile of the various types of compound classes within the sample. Various portions of the supercritical fluid chromatography output are assigned to specific types of molecules, such as paraffins, naphthenes that include various numbers of rings, and aromatics that include various numbers of aromatic rings. These general assignments are used to provide relative weightings for the amounts of each molecular type or compound class within a sample. The relative amounts of compounds within a given compound class are then assigned based on calibrations from the mass spectrometry measurements. All of this information is then fit to other bulk properties of the sample in order to arrive at a model of composition.

While the above technique provides a model of composition, a number of uncertainties remain in the quantitative values generated by the model. For example, a supercritical fluid chromatogram does not provide a clean distinction between some types of compound classes, such as multi-ring naphthenes versus 1-ring aromatics. As a result, assignment of the relative amounts of these two compound classes in a supercritical fluid chromatography spectrum is likely to result in some error relative to the actual composition. Additionally, assigning relative amounts within a compound class based on mass spectrometry is dependent on assuming that response factor for compounds within a given compound class is either constant or that it varies in a predictable manner. Some improvement in determination of relative amounts within a compound class can be achieved by continuing to perform calibrations of the field-ionization time-of-flight mass spectrometer using known samples, in order to obtain a table of representative response factors.

In various embodiments, quantitative characterization of a sample can be improved and/or simplified by using a combination of field-ionization time-of-flight mass spectrometry and 2-dimensional gas chromatography with flame ionization detection. As described above, the mass spectrometry is used to identify the various compounds within a sample. The 2-dimensional gas chromatography with flame ionization detection is then used to determine the amounts of each identified compound within a sample.

Using flame ionization as the detector for a separation is beneficial for identifying the amount of a compound that is present in a sample, but it does not directly provide any compositional information. However, 2-dimensional gas chromatography provides a detailed separation for the compounds within a sample. Based on this, quantitative analysis of the 2D-GC can be used to provide normalization targets for the field ionization time-of-flight mass spectrometer, including specific details on the normal paraffin carbon number distribution. This allows for matching of the quantitative information from the flame ionization detector with both the qualitative information (such as compositional information) and quantitative information of the field-ionization time-of-flight mass spectrometer.

Petroleum or Hydrocarbon Samples for Analysis

In this description, reference may be made to hydrocarbon streams, hydrocarbon samples, and/or hydrocarbon mixtures. Hydrocarbon streams, samples, or mixtures are defined herein to include streams, samples, or mixtures containing heteroatoms. As understood by those of skill in the art, a typical mineral petroleum feedstock often includes compounds containing heteroatoms, such as (but not limited to) compounds containing sulfur, nitrogen, trace metals, and/or oxygen. Unless it is specifically indicated otherwise, hydrocarbon streams, samples, or mixtures are defined to include streams, samples, or mixtures containing compounds that include such heteroatoms. Thus, even though a typical petroleum sample contains atoms other than carbon and hydrogen, such a petroleum sample is included in the definition of a hydrocarbon sample.

In various embodiments, petroleum and/or other hydrocarbon samples can be analyzed using a combination of field ionization time-of-flight mass spectrometry and 2-dimensional gas chromatography with flame ionization detection. For both of these analysis methods, at least one separation stage of gas chromatography is used to separate a sample to reduce the number of compounds reaching a corresponding detector at a given time. Thus, petroleum and/or other hydrocarbon samples that are characterized according to embodiments of the invention are preferably samples that are suitable for separation via gas chromatography. In some embodiments, the samples correspond to samples with a final boiling point of about 1050° F. (566° C.) or less. Such samples correspond to distillate samples that can include diesel boiling range compounds, atmospheric gas oil compounds, and vacuum gas oil compounds. Compounds with boiling points greater than 1000° F. (538° C.), such as greater than about 1050° F. (566° C.) or 1100° F. (593° C.), depending on the embodiment, correspond to compounds from vacuum resid. Due to the higher boiling point of vacuum resid compounds, the gas chromatography or the field ionization techniques used in the invention may not have full effectiveness.

In other embodiments, a sample for analysis can correspond to a diesel boiling range sample. Examples of diesel boiling range samples include samples with a boiling range from about 400° F. (204° C.) to about 800° F. (427° C.). In still other embodiments, if kerosene boiling range compounds are also included in the sample, the initial boiling point for the sample can be as low as at least about 215° F. (102° C.).

In this discussion, reference will be made to analyzing petroleum samples and/or hydrocarbon samples. A petroleum and/or hydrocarbon sample can be obtained in any convenient manner. An initial source for a sample can correspond to a raw or virgin mineral feed, a non-conventional feed such as a synthetic crude or a biologically derived oil, an output from a refinery process, or a combination of any of the above. When performing the combined analysis described herein, a single sample of a desired hydrocarbon for study can be obtained and then divided into multiple portions for analysis. Alternatively, multiple samples can be separately obtained from the initial hydrocarbon source. Still another option is to use any other convenient technique for providing samples to the analysis techniques. Of course, an "initial hydrocarbon source" can also be created by mixing portions from a plurality of hydrocarbon sources to create samples (or a source for samples).

In various embodiments, the combination of field ionization time-of-flight mass spectrometry analysis with 2-dimensional gas chromatography flame ionization detection analysis allows for construction of a model of composition for a sample from a given source. The model of composition can be constructed at a desired level of detail. One option is to construct the model of composition at the compound level, so that each compound is represented with a corresponding weight percent in the model.

Another option is to construct the model of composition based on compound classes. Compound classes refer to types of molecules within a sample (or an initial source.) Examples of compound classes include, but are not limited to, paraffins, one-ring naphthenes, two-ring naphthenes, other multi-ring naphthenes, 1-ring aromatics, two-ring aromatics, other multi-ring aromatics, and polar compounds. Grouping compounds into compound classes in the model of composition can facilitate analysis of the properties of a given composition. Additionally, compound classes can be used as an additional verification for a model of composition. For example, the total aromatics content of a hydrocarbon sample is a relatively routine test that can be performed on a sample. By organizing compounds according to compound class, a total aromatics measurement for a sample can be compared with the total number of aromatic compounds in the compound classes. If desired, the relative weight percentages of the compounds in the model of composition can be normalized to adjust the percentage of total aromatics versus the percentage of other types of compounds.

Still another option is to construct the model of composition by organizing compounds based on Z-number distribution. A Z-number is defined as hydrogen deficiency in the general chemical formula, $C_cH_{2c+z}N_nS_sO_o$. The more negative the Z-number, the more unsaturated the corresponding molecule. Based on the detailed compositional information available from the time-of-flight mass spectrometer, in combination with the compound class information available from the 2-dimensional gas chromatographic separation, the compounds within a sample can be organized based on the corresponding Z-class. This allows compounds to be grouped roughly according to compounds that form a homologous series within a sample. Yet another option is to use a combination of any convenient classification method, including the methods described above, for forming the model of composition.

Gas Chromatography with Field Ionization Time-of-Flight Mass Spectrometry

In various embodiments, two portions of a hydrocarbon sample are analyzed using complementary techniques. A first portion of the hydrocarbon sample is analyzed using a combination of gas chromatography (GC) to perform a separation followed by field ionization time-of-flight mass spectrometry (FI-TOF-MS) to characterize the material exiting from the gas chromatography process.

Gas chromatography is generally used to separate hydrocarbon species by boiling point or polarity depending on type of column used. For GC-FI-TOF mass spectrometry, a gas chromatography technique for separation based on boiling point is preferably selected.

In the various types of mass spectrometry, one of the requirements for detecting a compound is to form some type of ion. In field ionization, ions are formed by applying a high electric potential to a sharp surface. This results in an electric field near the surface that is suitable for forming ions of compounds, such as hydrocarbon compounds, that are on or near the surface. Field ionization is a method for forming ions that allows for "soft" ionization of hydrocarbon molecules. This means that the amount of fragmentation of hydrocarbon molecules due to the ionization is reduced or minimized. By using a soft ionization method, the number of peaks in the resulting mass spectrogram is reduced, which facilitates identification of compounds.

The compounds ionized by the field ionization are then detected using a time-of-flight mass spectrometer (TOF-MS). In various aspects, the time-of-flight mass spectrometer apparatus has sufficient resolution (mass resolving power>5000) to determine masses of hydrocarbons within 3 mDa or less, which allows for accurate determination of the elemental composition of species. This also allows the TOF-MS apparatus to distinguish between species that differ in mass by only a few mDa. As a result, molecules that share the same nominal mass but different in exact masses can be resolved. For example, the mass of a carbon atom differs from the mass of 12 hydrogen atoms by 93.9 mDa. This type of difference is readily resolved using the TOF-MS apparatus. For some harder to resolve molecular groupings, such as the 3.4 mDa difference between 3 carbon atoms versus a sulfur with 4 hydrogen atoms, the combination of the GC separation with the TOF-MS is usually sufficient to completely or partially resolve the difference. For molecules with identical chemical compositions, such as normal paraffins versus isoparaffins or olefins versus cycloparaffins, resolution of distinct species is dependent on the retention time in the GC separation. TOF MS also accurately determines the masses of the hydrocarbon components (with an error of less than 3 mDa).

Although field ionization time-of-flight mass spectrometry (FI-TOF-MS) is suitable for determining detailed information about the composition of species within a sample, the FI-TOF-MS method is not as effective for determining relative amounts of species within a sample. For example, the field ionization technique has widely differing response factors for different classes of compounds, such as paraffins versus aromatics. A response factor is a measure of how readily a compound will ionize so that the compound can then be detected using the time-of-flight mass spectrometer. Compounds such as paraffins tend to be difficult to ionize using soft ionization techniques, resulting in low response factors in comparison with aromatics and other more easily ionized compounds. Because of the varying response factors, it can be difficult to determine the relative amounts of compounds within a sample using FI-TOF-MS. This problem can be mitigated (but not cured) by calibration.

2-Dimensional Gas Chromatography with Flame Ionization Detector

In 2-dimensional gas chromatography, a pair of chromatography columns are used in order to perform a more thorough separation. For example, a first column can provide a separation based on boiling point while a second column provides separation based on polarity. During operation, the second column preferably performs a relatively fast separation as compared with the first column, in order to reduce or minimize any overlap between species that were effectively separated in the first column.

As noted above, the first separation stage can correspond to a GC separation stage based on boiling point. The second separation stage can then correspond to a GC separation based on another type of property, such as polarity. By performing a relatively strong separation in the first GC separation stage, at most only a few compounds will enter the second GC separation stage during any given time period. As a result, the separation strength required in the second stage is lower. Additionally, it is desirable to have the second GC separation stage operate quickly enough to avoid substantial residence overlap in the second GC separation stage of compounds that were effectively separated in the first separation stage. As an example, consider two compounds with sufficiently distinct boiling points that the compounds exit the first GC separation stage at substantially different times, such as 20 seconds apart. The second GC separation stage preferably has a residence time that is sufficiently short so that the compound that exits the first GC separation stage at a substantially later time do not have an opportunity to "catch up" to the earlier compound during the second GC separation stage. Of course, such crossover of compounds may still occur in the second GC separation stage if the compounds exit the first GC separation stage at similar times. This is not a problem, as the benefit of the second GC separation stage is to provide an additional separation for those compounds that exit the first GC stage at similar times. Instead, the goal of having the second GC separation stage operate relatively quickly is to reduce or minimize situations where compounds that are clearly distinct based on the first GC separation stage become mixed or merged together again in the second GC separation stage.

In various embodiments, the second GC separation stage can have a characteristic residence time on the order of seconds. For example, the longest residence time for compounds that are passed into the second GC separation stage from the first GC separation stage can be about 20 seconds or less, such as about 15 seconds or less or about 10 seconds or less. So long as the second GC separation stage is effective for providing additional separation, the minimum residence time for a compound to exit the second GC separation stage is not critical. For example, minimum residence times for compounds exiting the second GC separation stage of can be at least 0.1 seconds, such as at least 0.25 seconds or at least 0.5 seconds. Optionally, the minimum residence time for the second GC separation stage can also be characterized based on compounds with at least a threshold molecular weight, such as compounds with a molecular weight of at least 60 Daltons, such as at least 80 Daltons or at least 100 Daltons.

For comprehensive two-dimensional gas chromatography (GC×GC), a suitable system is an Agilent 6890 gas chromatograph (Agilent Technology, Wilmington, DE) configured with a split/splitless inlet, capillary columns, and detector. The capillary column system contains a first-dimensional column, which is a BPX-5, 30 m, 0.25 mm i.d., 1.0 µm film, and a second-dimensional column, which is a BPX-50, 2 m, 0.25 mm i.d., 0.25 µm film. Both columns are manufactured by SGE Inc. (Austin, Tex.). There is a looped jet thermal modulation assembly (Zoex Corp., Lincoln, Nebr.) located in between the first and the second dimension columns. This modulator assembly contains a liquid nitrogen cooled "trap-release" jet thermal modulator with a looped transfer column.

The detection system used for the 2D-GC measurements described herein was a flame ionization detector. Flame ionization is useful method for quantitative detection of the amount of carbon in a sample. In a flame ionization detector, a sample is passed through a flame formed from combustion of hydrogen and either oxygen or compressed air. This pyrolyzes the sample and generates ions based on the compounds (such as hydrocarbons) in the sample. The flame ionization is performed between two electrodes which serve as detectors. The signal generated from flame ionization is proportional to the mass of the hydrocarbons in the sample, which make the detector suitable for quantitative characterization.

Correlation of Chromatographic Columns

To provide both a qualitative and a quantitative characterization of a sample, the results from the GC-FI-TOF-MS are combined with the results from the 2D-GC flame ionization detector. In some aspects of the invention, the combination of results is further enhanced by determining a correlation between the initial GC separation of the FI-TOF-MS detector and the first stage separation of the 2D-GC.

One option for combining the results between the GC-FI-TOF-MS system and the 2D-GC system is to use sufficiently similar operating conditions for both the GC in the GC-FI-TOF-MS system and for the first GC separation stage in the 2D-GC system. Preferably, using substantially similar operating conditions can correspond to using the same type of chromatography column in both separations. By using the same type of column for both GC separations (along with an optional calibration), the compounds emerging from the GC in the mass spectrometry system should emerge at similar times and in similar orders as the compounds emerging from the first GC separation stage in the 2D-GC system.

In this type of option, combining the compositional information from the FI-TOF-MS system with the quantitative information from the 2D-GC system should be relatively straightforward. For the compositional information, the GC separation performed prior to the field ionization will result in a series of mass spectrographs that vary based on the mass of the compound(s) exiting the GC separation at a given time. At any given time, the mass spectrograph will only show a relatively small number of peaks, with the average number of peaks at a given time decreasing as the separation efficiency of the GC column increases. By using a mass spectrometer with sufficient resolving power, the compositional formulas of these compounds in the mass spectrum can be determined with a high degree of confidence. As noted above, this assignment of compositional formulas does not distinguish between true isomers, but it can distinguish between compounds with different chemical compositions that have only an approximate match in molecular weight.

In embodiments where the same type (or a sufficiently similar type) of columns are used for the GC separation for the FI-TOF-MS and for the first GC separation stage, the compounds detected by the mass spectrometer can also be expected to exit the first GC separation stage at a similar time and/or in a similar order. Because the FI-TOF-MS detector allows for accurate compositional information, it can be feasible to determine the order that the compounds detected in the mass spectrometer will exit from the second GC separation stage of the 2D-GC system. Optionally, all individual compounds in the FI-TOF-MS spectrum can be uniquely assigned to corresponding compounds exiting the second separation stage of the 2D-GC system. This would enable complete quantitative characterization of the compounds in a sample. Alternatively, the quantitative information from the 2D-GC system may be limited to determining the quantity for a group of molecules, such as a Z-class or a general grouping such as polars or saturates, or compound classes such as paraffins, naphthenes with various numbers of rings, aromatics with various numbers of rings, and polar molecules. Optionally but preferably, the quantitative information for a compound class generated by 2D-GC can be further divided into a plurality of retention windows within the class.

In other embodiments, the GC separation stage used for the GC-FI-TOF-MS analysis can be different from the first GC separation stage for the 2D-GC analysis. So long as the two GC separation stages can be sufficiently correlated, any convenient types of GC separation stages can be used for the initial GC separation of the GC-FI-TOF-MS analysis and for the first stage of the 2D-GC analysis. As described above, the compounds detected in the mass spectrometer can then be assigned to compound classes and then normalized based on the amount of each compound class detected based on the 2D-GC analysis. Optionally but preferably, the quantitative information for a compound class generated by 2D-GC can be further divided into a plurality of retention windows within the class.

Preferably, the GC separation stage for the FI-TOF-MS analysis can result in the same or a (substantially) similar exit order for compounds emerging from first GC separation stage. The residence times in the GC for the FI-TOF-MS analysis do not have to be the same as the residence times for the first separation stage of the 2D-GC analysis. However, it is preferable for the order of exit for the compounds to be similar.

Another option for correlation of the $1^{st}$ dimension of separation of GC-FI-TOF and 2DGC analysis can be based on alignment of the $1^{st}$ dimension of separation based on time windows defined by the elution time for normal paraffins within the $1^{st}$ separation dimension for the two chromatography methods. During 2D-GC with flame ionization detection, the peaks in the spectrum corresponding to paraffins can be readily identified. Due to the relatively low number of potential paraffin structures, the peaks within the paraffin portion of the 2D-GC spectrum can be specifically correlated with likely paraffin structure, based on elution time in the first gas chromatography column. The paraffins in the FI-TOF-MS spectrum can also be readily identified based on molecular weight. Because the paraffins within both spectra can be identified, the relative elution times of the paraffins can be compared between the 2D-GC and FI-TOF-MS systems in order to correlate the gas chromatography columns in the respective systems.

One option for comparing two different separations is to use a retention normal-paraffin index to align the two separations. The retention normal-paraffin index is defined as the retention time of a normal paraffin containing a given number of carbons for a particular separation. For example, retention normal-paraffin index 8 is the retention time of n-octane (which contains 8 carbons) in a given separation. Similarly, retention normal-paraffin index 9 corresponds to the retention time of n-nonane. The absolute value of the retention time for a given n-paraffin can vary between different separation columns and/or operating conditions. However, for separation columns that produce the same or a similar order of exit for compounds in a sample, characterizing the retention time based on retention normal-paraffin index values allows for a comparison between different separation columns (or similar columns operated under different conditions).

Based on the measurable values for the various n-paraffins, other types of characterizations can be developed for a separation. For example, a retention normal-paraffin index of 8.5 can be identified as the average of the retention normal-paraffin index values at indexes 8 and 9. Additionally, the retention normal-paraffin index values can be used to define retention windows for the compounds eluting in a separation column. For example, the elution time between retention normal-paraffin indexes 8 and 9 in a separation can be defined as a time window, so that compounds within the time window can be characterized together. For a technique such as 2DGC, identifying such a time window can allow for quantitative characterization of the amount of various compound classes that elute within a time window. This quantitative characterization can then be used to normalize the signal values from a technique such as GC-FI-TOF based on the compound class corresponding to the molecular formulas assigned to the various peaks.

In a comparison of the $1^{st}$ dimension of separation for GC-FI-TOF and 2DGC, an initial step can correspond to aligning the elution sequences for the two columns. The separation data for the $1^{st}$ dimension of separation for each column can then be divided into time slices (or windows) based on the retention normal-paraffin index for each column. For example, the GC-FI-TOF data can be averaged across the time interval between retention normal-paraffin index 11 and 12. A molecular composition can then be generated for the time interval. The 2DGC data can then be similarly averaged across the time same retention window interval to generate compound classes. Based on the retention window for the 2DGC data, the molecular composition from the GC-FI-TOF data can be normalized based on the quantitative information regarding compound classes in the same retention window from the 2DGC. The process is repeated for the entire $1^{st}$ dimension elution. The total composition can then be derived by combining data from all of the retention windows.

Normalization of FI-TOF-MS Data Based on 2D-GC Data

Figure 3:
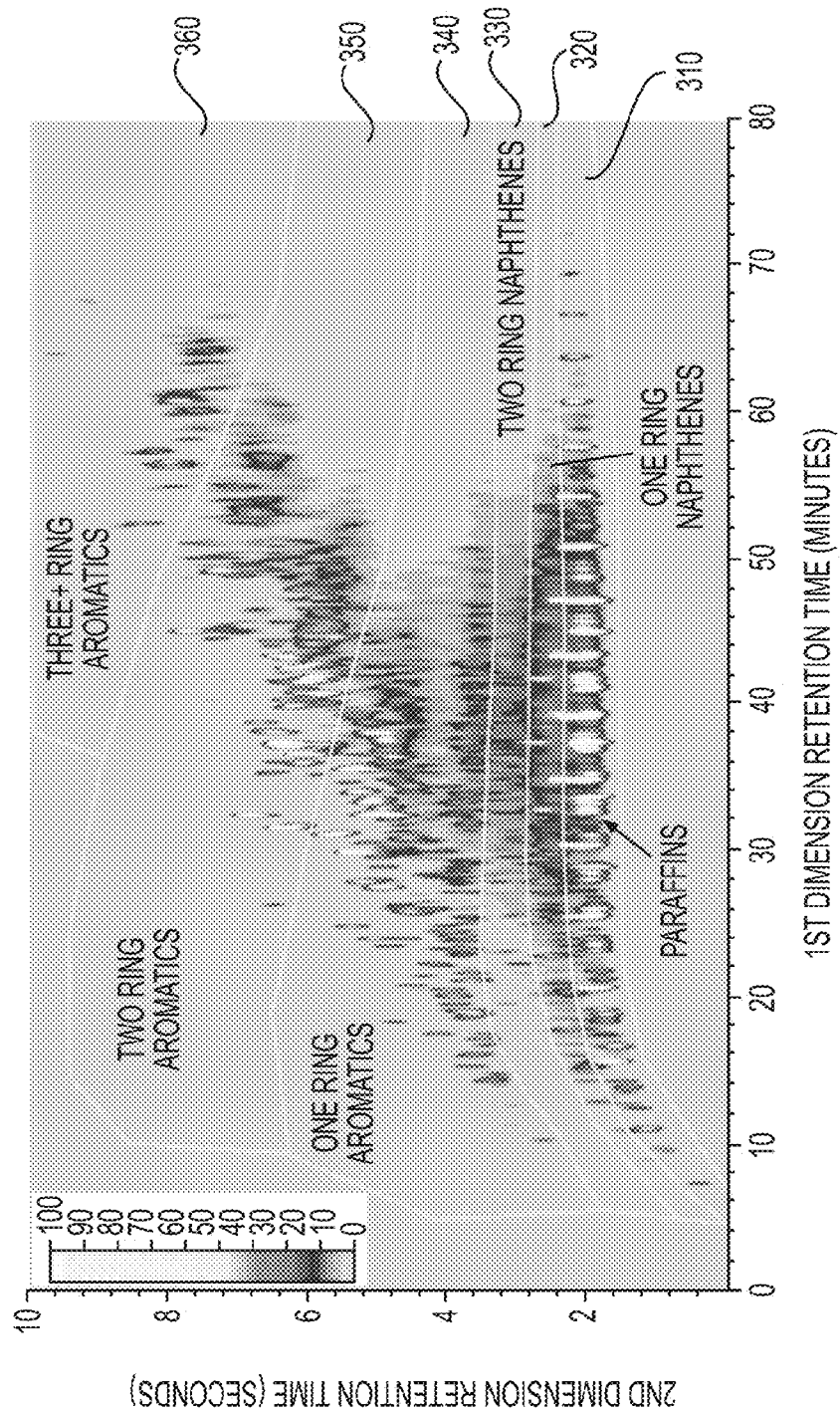
FIG. 3 shows a 2D-gas chromatogram based on flame ionization detection of a diesel boiling range sample.

FIG. 3 shows an example of the output generated by performing 2D-GC with flame ionization detection on a diesel sample. In FIG. 3, the horizontal axis represents the retention time for the first gas chromatography column of the 2D-GC apparatus, while the vertical axis corresponds to the second gas chromatography column. As shown in FIG. 3, the compounds detected by flame ionization detection can be grouped into a plurality of categories or classes, based on exit time from the second dimension of the 2D-GC. The fastest compounds to emerge from the 2D-GC are paraffins 310, followed by 1-ring naphthenes 320, 2-ring naphthenes 330, 1-ring aromatics 340, 2-ring aromatics 350, and 3-ring aromatics 360. Of course, additional classes of compounds could be present in a higher boiling range sample, such as a sample based on a whole crude instead of a sample based on just a diesel fraction.

Based on the assignment of peaks in the 2D-GC into classes, the peaks within each class can be added together to generate an overall amount of each class present in the sample. For a sample with an end boiling point below 1050° F. (566° C.), it will typically be expected that all of the sample will be able to emerge from the gas chromatography columns, so that the detected amounts for each compound class will correspond to the entire sample. Based on this, the detected amounts for each compound class relative to the total sample can be determined.

After generating a normalization value for each sample, the normalization values can be applied to the detected intensities for compounds from the GC-FI-TOF-MS. Based on the assignment of molecular formulas, the compounds detected by FI-TOF-MS can be assigned to compound classes that match the general classes identified in the 2D-GC. Within a given class of compounds, such as 1-ring aromatics, it is expected that the response curve for different compounds will be relatively uniform. Based on the 2D-GC data, the relative amount of each class within a sample is known. Using the 2D-GC data to provide the total amount of compounds within a class, the relative peak heights of the compounds within the class, as detected by FI-TOF-MS, can be normalized so that the sum of the normalized FI-TOF-MS peaks corresponds to the amount of the overall compound class that is present within the sample. By using this type of normalization, an amount for each type of compound can be identified without having to strictly correlate the peaks in the 2D-GC with the individual composition peaks in the FI-TOF-MS. The normalized amounts for the compounds within the sample can then be used, for example, as a basis for predicting other properties of the sample.

In some optional but preferred aspects of the invention, normalizing based on compound class can be augmented by normalizing based on both compound class and a retention time window or slice for the first gas chromatography stage in the 2D-GC. In this optional aspect, the compounds detected by the 2D-GC with flame ionization detection are still grouped according to compound class as described above. Additionally, within each compound class, retention window groups are formed based on the amount of time required for a compound to elute in a gas chromatography stage.

The retention window groups within the compound classes can be drawn in any convenient manner. One option is to define common retention window groups that are used across multiple compound classes, such as common retention window groups that are used for all compound classes. Time windows based on retention normal-paraffin index values are an example of time windows that can be suitable for dividing a chromatograph into manageable pieces for analysis. Another option is to define different retention window groups for each compound class. The size of a retention window group can be selected based on any convenient criteria. One option is to define a retention window based on an amount of elution time in a gas chromatography column. Another option is to define retention windows so that the amount of time can vary, but a specified number of compounds reside within each retention window. The retention windows can be defined based on the first stage of the 2D-GC or based on the GC stage of the FI-TOF-MS detector.

After defining a retention window, the peaks within a retention window for a compound class in the 2D-GC can be used to normalize the measured peaks for the corresponding compounds within the retention window from the FI-TOF-MS. For example, the peak values within a compound class in a retention window can be combined, so that normalization is performed using the aggregated value for a compound class. Because the normalization is performed based on both compound class and retention time, at least some correlation of the first stage of the 2D-GC with the gas chromatograph of the FI-TOF-MS detector is required. As described above, the retention times for the stages do not have to be the same, so long as the order of exit of the stages can be sufficiently correlated. The stages from the 2D-GC and the FI-TOF-MS can be correlated based on using the same type of gas chromatography stage; based on correlation of retention times for specifically identified paraffin compounds between the stages; or by any other convenient method.

It is noted that because the retention times in the 2D-GC and the FI-TOF-MS are not necessarily the same, the retention windows will typically be defined based on one of the detection methods, such as the retention time for the first stage of the 2D-GC. For example, after determining the size of the retention window based on the first stage of the 2D-GC, the number of compounds within a compound class that are also within a given retention window can be calculated. A corresponding retention window for the FI-TOF-MS can then be determined, for example, by drawing a retention window to capture the same number of compounds as the number calculated for the corresponding 2D-GC retention window. Because both detection methods exhibit little or no baseline rise, the number of distinct compounds should be clear in both methods, thus allowing the retention window correlation to be made even though the elution times for the gas chromatography stages may not be identical. Optionally but preferably, another alternative for identifying a corresponding retention window is to draw retention windows based on the same retention normal-paraffin index values for both separations.

It is noted that about 1050° F. is the upper limit for boiling point for the types of compounds that can be characterized using the FI-TOF-MS detection method. This is due in part to a limited ability/inability to cause such heavier compounds to pass through a gas chromatography column. For a sample containing such 1050° F.+compounds, the lower boiling portion of the sample can still be quantitatively characterized by using a reference sample. A reference sample can correspond to any convenient sample where the entire sample can be detected using the 2D-GC technique. For such a sample, the detected peak heights in the 2D-GC spectra can be integrated to determine an overall signal intensity for a given volume of sample. The expected overall signal intensity for a given volume of sample can then be compared with the measured signal intensity for a new or unknown sample that may contain 1050° F.+material. The difference in measured signal intensity for a given volume between the reference sample and the new sample corresponds to the amount of material in the new sample that does not pass through the gas chromatography column(s).

After determining the amount of material in a sample that cannot be characterized, the portion of the sample that can be measured is characterized as described above, with the understanding that the normalized FI-TOF-MS peaks represent less than all of the sample. If it is desired to develop a model of composition for the remaining portion of the sample, that can be performed in any convenient way, with the amount of material not detected being used to normalize the amounts for any compounds assigned to the remaining portion of the sample.

EXAMPLE

Comparison of Supercritical Fluid Chromatography with Flame Ionization Detection (1D-GC and 2D-GC)

In various embodiments, an improved method for characterizing a petroleum sample (or other hydrocarbon sample) is provided by using a combination of a field ionization time-of-flight mass spectrometer (FI-TOF-MS) and a two dimensional gas chromatograph (2D-GC) with a flame ionization detector to analyze a sample. The two techniques are combined by correlating the gas chromatograph used as the input for the FI-TOF-MS with the first separation stage of the 2D-GC. Part of the benefit achieved by this method is the benefit derived from using flame ionization as the detection method for the output from the 2D-GC separation. This correlation allows the compositional information determined in the FI-TOF-MS analysis to be matched with quantitative information from the flame ionization.

The benefit of using flame ionization as a detection method can be seen in comparison with using supercritical fluid chromatography to provide quantitative information. Like gas chromatography, supercritical fluid chromatography is a separation technique. SFC is a normal phase chromatographic technique that utilizes high pressure liquid carbon dioxide as the mobile phase. Supercritical fluid chromatography cannot be used with a mass spectrometer, and also cannot be readily compared with the gas chromatographs used to provide an initial separation for mass spectrometry. However, supercritical fluid chromatography does provide some of the quantitative information that is available via 2D-GC with flame ionization detection.

FIG. 1 shows a typical supercritical fluid chromatogram or trace. Non-polar components elute first, followed by components of increasing polarity. Prior studies have defined the saturate splits while the aromatic splits are defined by a UV detector monitoring four wavelengths that are believed to be representative of one to four ring aromatics. Quantitative information can be derived from the supercritical fluid chromatogram by assigning the area under the trace to various components. This allows for a relative determination of the amounts of classes of compounds within a sample, such as paraffins, one-ring naphthenes, or two-ring aromatics. This can be used in combination with a technique such as FI-TOF-MS by assuming that the response of compounds within a class will be roughly constant in FI-TOF-MS. The FI-TOF-MS data would then be used to assign quantitative information within a class, while the supercritical fluid chromatography data would allow for normalization of quantities between classes.

In supercritical fluid chromatography, errors become significant as the valleys between the paraffins and one-ring naphthenes, and the one-ring naphthenes and two-ring naphthenes rise. Because the supercritical fluid chromatogram does not allow for distinctions between individual compounds, the area under the trace in a supercritical fluid chromatogram is assigned to classes by splitting the area under the trace with a vertical line between two regions. In addition to difficulties in selecting where to draw such a vertical line, this ignores the likely Gaussian nature of peaks for adjacent classes. Integration errors for the area under the trace can also occur in the aromatics region of the trace. The ring class separation is based on UV response at different wavelengths, but there is usually significant overlap between aromatic classes as well, especially at higher retention times (i.e. higher ring classes).

Using 2D-GC with flame ionization detection provides superior quantitative information relative to supercritical fluid chromatography methods for at least two reasons. First, by using 2D-GC with flame ionization detection, less reliance is placed on the quantitative information from the FI-TOF-MS. For the supercritical fluid chromatography method described above, an assumption is made that FI-TOF-MS response curves are uniform across compound classes. By contrast, when the FI-TOF-MS is paired with 2D-GC with flame ionization detection, the only assumption required is that response curves within a compound class are similar, which is believed to be more reliable assumption. This reduces or minimizes the quantitative errors that result from the assumption of uniform response curves for compounds within classes. Second, the 2D-GC with flame ionization detection method provides more detailed quantitative information, allowing for improved accuracy in determining the amounts for each class of compounds.

Figure 2:
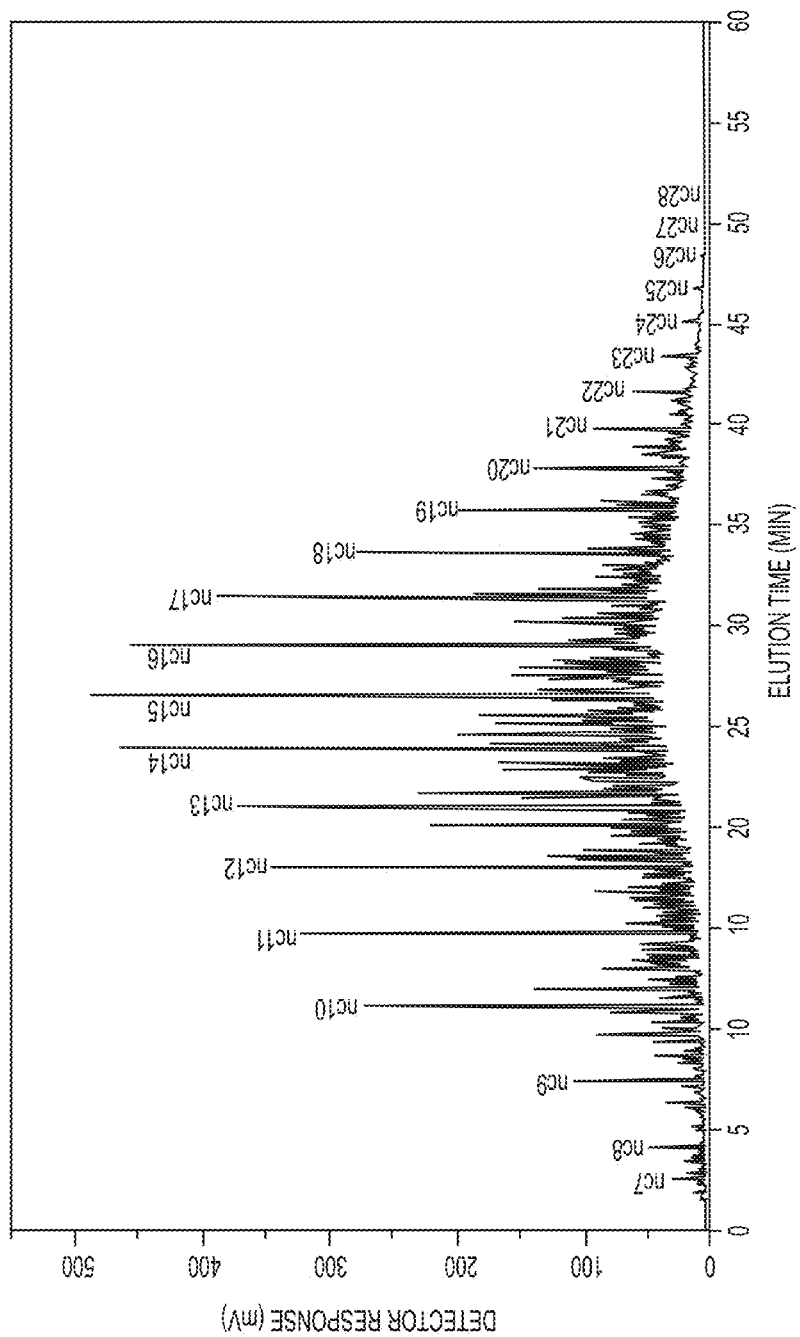
FIG. 2 shows a 1D-gas chromatogram based on flame ionization detection of a diesel boiling range sample.

FIG. 2 shows an example of an analysis of a typical diesel boiling range sample using 1D-GC with flame ionization detection as the analysis method. In contrast to the supercritical fluid chromatogram, the flame ionization spectrum in FIG. 2 shows distinct peaks for the various compounds in the sample. This allows for integration of the area under the trace for individual compounds, which can then be summed (if desired) to derive the amounts for compound classes. Thus, flame ionization detection allows for more detailed quantitative analysis than supercritical fluid chromatography.

One potential shortcoming of the spectrum shown in FIG. 2 is the presence of baseline rise, which is due in part to the overlapping exit times of compounds from the 1D-GC separation. This potential shortcoming can be mitigated by using a 2D-GC separation as the input for the flame ionization detection. FIG. 3 shows an example of the separation that can be achieved for another typical diesel boiling range sample. In FIG. 3, retention times are shown for both first separation stage and the second separation stage of the of the 2D-GC technique. At a given combination of retention times for the first separation stage and the second separation stage, an intensity is available which corresponds to the amount of hydrocarbon detected at that time. Based on the nature of the second separation stage, FIG. 3 also shows a rough assignment of the data into compositional classes, such as paraffins, one-ring naphthenes, or two-ring aromatics. Because the second separation stage provides further separation of compounds that emerge from the first separation stage at similar times, the 2D-GC separation reduces the amount of baseline elevation. This allows for better assignment of quantitative information to the proper compound in a sample.

FIGS. 1 to 3 demonstrate the improvement that can be achieved using 2D-GC with flame ionization detection for quantitative analysis of the compounds within a petroleum (or other hydrocarbon) sample. Further evidence of this improvement is provided in Table 1 below. Table 1 shows a comparison of the quantitative information derived using supercritical fluid chromatography versus 2D-GC with flame ionization detection as a complementary technique for FI-TOF-MS. A typical diesel boiling range sample was used for the comparison in Table 1.

Table 1 shows the assignment of chemical class "lumps" for the diesel sample using both supercritical fluid chromatography (SFC) and 2D-GC with flame ionization detection.

TABLE 1

Comparison of 2D-GC and SFC

| Fraction | Normalized 2D-GC | Normalized SFC |
|---|---|---|
| Paraffins | 26.74 | 26.60 |
| One-Ring Naphthenes | 15.63 | 12.34 |
| Two+-Ring Naphthenes | 7.84 | 14.52 |
| One-Ring Aromatics | 24.78 | 22.35 |
| Two-Ring Aromatics | 20.29 | 14.08 |
| Three+-Ring Aromatics | 4.72 | 10.10 |
| Total | 100 | 100 |

As shown in Table 1, the total values for saturates (paraffins plus naphthenes) and aromatics are similar for 2D-GC and SFC. However, when further broken down into compound classes, SFC shows significant differences in the 2+ring naphthenes as well as the higher ring aromatics. Due in part to the superior baseline resolution available in 2D-GC with flame ionization detection, it is believed that the 2D-GC values are more reliable.

Table 2 shows the benefit of using 2D-GC instead of 1D-GC as the separation method for the flame ionization detector for the same type of diesel sample shown in Table 1. In Table 2, the relative amounts of various n-paraffins in the diesel sample are shown. In Table 2, "nP-Cx" refers to a normal paraffin containing "x" number of carbons. For most paraffins, the 1D-GC and 2D-GC methods provide similar amounts. However, in the 1 D-GC analysis, a somewhat large error is present for the amount of the C17 normal paraffin. This is due to an overlap of an aromatic compound with the C17 paraffin in the 1D-GC flame ionization detection trace. By contrast, in the 2D-GC trace, the second separation stage causes the aromatic compound to arrive at the flame ionization detector at a later (distinct) time, so that the C17 paraffin peak is not convoluted with the aromatic peak.

TABLE 2

Comparison of 1D-GC and 2D-GC with FID

| Carbon Number | Normalized 2DGC | GC-FID |
|---|---|---|
| nP-C9 | 0.18 | 0.27 |
| nP-C10 | 0.67 | 0.83 |
| nP-C11 | 0.96 | 1.06 |
| nP-C12 | 0.96 | 1.25 |
| nP-C13 | 1.23 | 1.24 |
| nP-C14 | 1.91 | 1.84 |
| nP-C15 | 2.05 | 1.95 |
| nP-C16 | 1.91 | 1.64 |
| nP-C17 | 2.12 | 1.39 |
| nP-C18 | 1.19 | 0.92 |
| nP-C19 | 0.65 | 0.57 |
| nP-C20 | 0.4 | 0.36 |
| nP-C21 | 0.27 | 0.26 |
| nP-C22 | 0.17 | 0.15 |
| nP-C23 | 0.1 | 0.10 |
| nP-C24 | 0.05 | 0.05 |
| nP-C25 | 0.02 | 0.03 |
| nP-C26 | 0.01 | 0.01 |
| Total | 14.87 | 13.92 |

Assignment of Compounds to Z-Classes

In some aspects of the invention, the output from the 2D-GC with flame ionization detection is used to quantitatively determine the amount of each compound class present within a petroleum (or other hydrocarbon) sample. The output from the FI-TOF-MS analysis can then be used to assign detected compounds to a corresponding compound class. One option for assignment of compounds to compound classes is to assign based on a Z-class, where the Z-class defines the number of ring structures and/or degrees of unsaturation present in a compound. FIG. 4 shows the Z-class for various representative compounds containing only carbon and hydrogen. FIGS. 5 and 6, respectively, show the Z-class for various representative compounds that also include either one sulfur atom or two sulfur atoms.

Additional Embodiments

Embodiment 1. A method for characterizing petroleum or other hydrocarbon compositions, comprising: separating a first plurality of compounds in a first hydrocarbon sample using a first gas chromatography separation; determining a composition and a first weight for each of the separated first plurality of compounds using mass spectrometry, the ions for mass spectrometry being formed by a soft ionization method; separating a second plurality of compounds in a second hydrocarbon sample using a second gas chromatography separation, the second gas chromatography separation including at least a first separation stage and a second separation stage, the second hydrocarbon sample being derived from the same hydrocarbon source as the first hydrocarbon sample; determining a second weight for each of the separated second plurality of compounds; assigning the separated second plurality of compounds to a plurality of compound classes; determining a relative weight for each of the plurality of compound classes based on the second weights of the assigned compounds for each compound class; normalizing the first weight for each of at least a portion of the first separated plurality of compounds, based on the determined relative weights for the plurality of compound classes, to generate a normalized weight for each compound, the normalizing of a first weight for a compound being based on at least a compound class corresponding to a determined composition for the compound; and developing a model of composition for the hydrocarbon source based on at least the normalized weights for the first separated plurality of compounds.

Embodiment 2. The method of Embodiment 1, further comprising identifying and quantifying a composition for one or more paraffin compounds in the separated second plurality of compounds.

Embodiment 3. A method for characterizing petroleum or other hydrocarbon compositions, comprising: separating a first plurality of compounds in a first hydrocarbon sample using a first gas chromatography separation, each compound in the first plurality of compounds being within a retention normal-paraffin index window; determining compositions for the separated first plurality of compounds using mass spectrometry, the ions for mass spectrometry being formed by a soft ionization method; separating a second plurality of compounds in a second hydrocarbon sample using a second gas chromatography separation, the second gas chromatography separation including at least a first separation stage and a second separation stage, the second hydrocarbon sample being derived from the same hydrocarbon source as the first hydrocarbon sample, each compound in the second plurality of compounds corresponding to a compound in the first plurality of compounds, where each compound in the second plurality of compounds is within the same retention normal-paraffin index window as the corresponding compound in the first plurality of compounds; determining relative weights for the separated second plurality of compounds; correlating the first plurality of compounds with the second plurality of compounds; and developing a model of composition for the hydrocarbon source based on the correlation of the first plurality of compounds with the second plurality of compounds, and based on combining the determined compositions for the first plurality of compounds to provide a total composition.

Embodiment 4. The method of Embodiment 3, wherein the normalizing of a first weight for a compound is further based on a retention window corresponding to the determined compound.

Embodiment 5. The method of Embodiment 3 or 4, wherein correlating the first plurality of compounds with the second plurality of compounds comprises correlating the order of exit of the separated first plurality of compounds from the first gas chromatography separation with the order of exit of the separated second plurality of compounds from the second gas chromatography separation.

Embodiment 6. The method of any of Embodiments 3, 4, or 5, wherein correlating the first plurality of compounds with the second plurality of compounds comprises correlating the order of exit of the separated first plurality of compounds from the first gas chromatography separation with the order of exit of the separated second plurality of compounds from the first separation stage of the second gas chromatography separation.

Embodiment 7. The method of any of the above embodiments, wherein the second weight for each of the separated second plurality of compounds is determined by flame ionization detection.

Embodiment 8. The method of any of the above embodiments, wherein the separated second plurality of compounds are assigned to compound classes based at least in part on a number of naphthene rings in a compound, a number of aromatic rings in a compound, or a combination thereof.

Embodiment 9. The method of any of the above embodiments, wherein the second hydrocarbon sample comprises one or more additional compounds different from the second plurality of compounds, the method further comprising: calculating a combined weight for the separated second plurality of compounds based on the determined second weights; and calculating a weight percentage for the second plurality of compounds in the second hydrocarbon sample based on the combined weight for the separated second plurality of compounds, a weight of the second hydrocarbon sample, a weight of a reference sample, and a reference weight of a third plurality of compounds separated from the reference sample using the second gas chromatography separation.

Embodiment 10. The method of any of the above embodiments, wherein the model of composition is further based on one or more additional measured properties of a sample derived from the hydrocarbon source.

Embodiment 11. The method of any of the above embodiments, wherein developing the model of composition comprises assigning the plurality of compounds in the first hydrocarbon sample to a plurality of Z-classes.

Embodiment 12. The method of any of the above embodiments, wherein the final boiling point of the first hydrocarbon sample is about 1050° F. (566° C.) or less.

Embodiment 13. The method of any of the above embodiments, further comprising: obtaining an initial sample from the hydrocarbon source; and splitting the initial sample into at least the first hydrocarbon sample and the second hydrocarbon sample.

What is claimed is:

1. A method for characterizing petroleum or other hydrocarbon compositions, comprising:
    separating a first plurality of compounds in a first hydrocarbon sample using a first gas chromatography separation;
    determining a composition and a first weight for each of the separated first plurality of compounds using field ionization time of flight mass spectrometry;
    separating a second plurality of compounds in a second hydrocarbon sample using a second gas chromatography separation, the second gas chromatography separation including at least a first separation stage and a second separation stage, the second hydrocarbon sample being derived from the same hydrocarbon source as the first hydrocarbon sample;
    determining a second weight for each of the separated second plurality of compounds; wherein the second weight for each of the separated second plurality of compounds is determined by flame ionization detection;
    assigning the separated second plurality of compounds to a plurality of compound classes;
    determining a relative weight for each of the separated second plurality of compound classes based on the second weights of the assigned compounds for each compound class;
    correlating the first plurality of compounds with the second plurality of compounds; and
    normalizing the first weight for each of at least a portion of the separated first plurality of compounds, based on the determined relative weights for the plurality of compound classes, to generate a normalized weight for each compound, the normalizing of a first weight for a compound being based on at least a compound class corresponding to a determined composition for the compound; and
    developing a model of composition for the hydrocarbon source based on at least the normalized weights for the separated first plurality of compounds.

2. The method of claim 1, further comprising:
  obtaining an initial sample from the hydrocarbon source; and
  splitting the initial sample into at least the first hydrocarbon sample and the second hydrocarbon sample.

3. The method of claim 1, wherein the separated second plurality of compounds are assigned to compound classes based at least in part on a number of naphthene rings in a compound, a number of aromatic rings in a compound, or a combination thereof.

4. The method of claim 1, further comprising identifying and quantifying a composition for one or more paraffin compounds in the separated second plurality of compounds.

5. The method of claim 1, wherein the second hydrocarbon sample comprises one or more additional compounds different from the second plurality of compounds, the method further comprising:
  calculating a combined weight for the separated second plurality of compounds based on the determined second weights; and
  calculating a weight percentage for the second plurality of compounds in the second hydrocarbon sample based on the combined weight for the separated second plurality of compounds, a weight of the second hydrocarbon sample, a weight of a reference sample, and a reference weight of a third plurality of compounds separated from the reference sample using the second gas chromatography separation.

6. The method of claim 1, wherein the model of composition is further based on one or more additional measured properties of a sample derived from the hydrocarbon source.

7. The method of claim 1, wherein developing the model of composition comprises assigning the plurality of compounds in the first hydrocarbon sample to a plurality of Z-classes.

8. The method of claim 1, wherein the final boiling point of the first hydrocarbon sample is about 1050° F. (566° C.) or less.

9. The method of claim 1, wherein the normalizing of a first weight for a compound is further based on a retention window corresponding to the determined compound.

10. The method of claim 1, wherein correlating the first plurality of compounds with the second plurality of compounds comprises correlating the order of exit of the separated first plurality of compounds from the first gas chromatography separation with the order of exit of the separated second plurality of compounds from the second gas chromatography separation.

11. The method of claim 1, wherein correlating the first plurality of compounds with the second plurality of compounds comprises correlating the order of exit of the separated first plurality of compounds from the first gas chromatography separation with the order of exit of the separated second plurality of compounds from the first separation stage of the second gas chromatography separation.

12. The method of claim 1, wherein developing the model of composition further comprises normalizing at least a portion of the model of composition based on one or more additional measured properties of a sample derived from the hydrocarbon source.

13. The method of claim 1, wherein developing the model of composition comprises assigning the plurality of compounds in the first hydrocarbon sample to a plurality of compound classes.

14. The method of claim 1, wherein developing the model of composition comprises assigning the plurality of compounds in the first hydrocarbon sample to a plurality of Z-classes.

15. The method of claim 1, wherein the final boiling point of the first hydrocarbon sample is about 1050° F. (566° C.) or less.

* * * * *